United States Patent [19]

Ames et al.

[11] Patent Number: 5,916,912

[45] Date of Patent: Jun. 29, 1999

[54] DIETARY COMPOSITION FOR ENHANCING METABOLISM AND ALLEVIATING OXIDATIVE STRESS

[75] Inventors: Bruce N. Ames; Tory M. Hagen, both of Berkeley, Calif.

[73] Assignee: The Regents of the University of California, Oakland, Calif.

[21] Appl. No.: 08/874,467

[22] Filed: Jun. 16, 1997

[51] Int. Cl.⁶ .................................................. A61K 31/385
[52] U.S. Cl. .......................................... 514/440; 514/561
[58] Field of Search ...................................... 514/440, 561

[56] References Cited

U.S. PATENT DOCUMENTS 4,599,232 7/1986 Bertelli ....................................... 424/94
5,292,538 3/1994 Paul et al. .................................. 426/74
5,560,928 10/1996 DeFelice .................................. 424/466

OTHER PUBLICATIONS

Medical Hypotheses, McCarty; vol. 7, pp. 520–521, 1981.

Primary Examiner—Rebecca Cook
Attorney, Agent, or Firm—Richard Aron Osman

[57] ABSTRACT

The metabolic rate of aged cells of a mammalian host is enhanced without a concomitant increase in metabolic production of reactive oxygen species by orally administering to the host an effective dosage of a carnitine, such as acetyl-L-carnitine, and a mitochondrially active antioxidant, such as lipoic acid.

10 Claims, No Drawings

DIETARY COMPOSITION FOR ENHANCING METABOLISM AND ALLEVIATING OXIDATIVE STRESS

This invention was made with Government support under Grant (Contract) Nos.: CA39910 and ES01896 awarded by the National Institutes of Health to Professor Bruce Ames. The Government has certain rights to this invention.

INTRODUCTION

1. Field of the Invention

The field of the invention is dietary compositions and methods for modifying both cellular metabolism and the metabolic production of reactive oxygen species.

2. Background of the Invention

Numerous lines of evidence suggest that the organelles of cellular respiration, the mitochondria, decay with cellular aging (Shigenaga et al. 1994, PNAS 91, 10771). Unfortunately, the study of mitochondrial aging has been hampered because mitochondria isolated from older cells and host animals are fragile and heterogeneous. Hence the interpretation of any results is suspect as about half the mitochondria lyse during isolation. Our laboratory recently described a new method for studying mitochondria in hepatocytes from old animals that avoids this problem (Hagen et al. 1997, PNAS 94, 3064–3069). We found that mitochondria from older animals are not only more fragile, but have about half the level of cardiolipin, a key lipid unique to mitochondria, without which they can not maintain a high membrane potential. Furthermore, Hagen et al. show that in hepatocytes from older animals, the mitochondria are lower in membrane potential and leak out more toxic oxidants.

SUMMARY OF THE INVENTION

We have found that carnitine (a normal mitochondrial metabolite used to transport fatty acids into the mitochondria as fuel) and carnitine derivatives, when put into the drinking water of old animals, restore the cardiolipin and membrane potential of their mitochondria. At the same time, the carnitines increase the flux of reactive oxygen species from the mitochondria. We have found that we can specifically alleviate this enhanced flux with mitochondrially active antioxidants, such as lipoic acid. The two reagents given to old animals, restored all three mitochondrial functions and reversed several gross indicia of aging, including activity, muscle tone, coat appearance and kidney morphology.

Carnitine and carnitine derivatives have been used as metabolites in animal husbandry and for human diet and therapy. U.S. Pat. No. 5,362,753 (Method of increasing the hatchability of eggs by feeding hens carnitine); U.S. Pat. No. 4,687,782 (Nutritional composition for enhancing skeletal muscle adaptation to exercise training); U.S. Pat. No. 5,030,458 (Method for preventing diet-induced carnitine deficiency in domesticated dogs and cats); U.S. Pat. No. 5,030,657 (L-carnitine supplemented catfish diet); U.S. Pat. No. 4,343,816 (Pharmaceutical composition comprising an acyl-carnitine, for treating peripheral vascular diseases); U.S. Pat. No. 5,560,928 (Nutritional and/or dietary composition and method of using the same); U.S. Pat. No. 5,504,072 (Enteral nutritional composition having balanced amino acid profile); U.S. Pat. No. 5,391,550 (Compositions of matter and methods for increasing intracellular ATP levels and physical performance levels and for increasing the rate of wound repair); U.S. Pat. No. 5,240,961 (Method of treating reduced insulin-like growth factor and bone loss associated with aging); etc.

Similarly, mitochondrially active antioxidants including vitamins (especially C, E, B and D), glutathione, N-acetyl cysteine, lipoic acid, etc., have been used variously as human nutritional supplements and in dietary prophylaxis and therapy. For example, applications of lipoic acid have include U.S. Pat. No. 5,607,980 (Topical compositions having improved skin); U.S. Pat. No. 5,472,698 (Composition for enhancing lipid production in skin); U.S. Pat. No. 5,292,538 (Improved sustained energy and anabolic composition and method of making); U.S. Pat. No. 5,536,645 (Nutritive medium for the culture of microorganisms); U.S. Pat. No. 5,326,699 (Serum-free medium for culturing animal cells); etc.

These reagents, however, have never been administered in the combinations and dosages necessary to effect enhanced metabolic processes and simultaneously alleviate the resultant increase in oxidative stress. In general, the disclosed methods involve increasing the metabolic rate of aged cells of a mammalian host without a concomitant increase in metabolic production of reactive oxygen species by orally administering to the host an effective dosage of at least about 10 mg/kg host/day of a carnitine and at least about 10 mg/kg host/day of a mitochondrially active antioxidant. In preferred embodiments, the carnitine is acetyl-L-carnitine and the antioxidant comprises a metabolically reactive thiol group and is preferably lipoic acid. The invention also provides orally administratable unit dosages comprising at least about 250 mg/kg host/day of a carnitine and at least about 250 mg/kg host/day of a mitochondrially active antioxidant.

DETAILED DESCRIPTION OF SPECIFIC EMBODIMENTS OF THE INVENTION

Methods for making and preparing carnitine and active carnitine derivatives are known in the art, e.g. U.S. Pat No.: 4,766,222 (Novel class of acyl-derivatives of carnitine process for preparing same and therapeutic use thereof); U.S. Pat. No. 4,673,534 (Carnitine salts particularly suitable for oral use); U.S. Pat. No. 4,743,621 (Ester of acetyl carnitine, processes for its preparation and pharmaceutical compositions containing it); U.S. Pat. No. 4,593,043 (Mercapto acyl-carnitines and pharmaceutical compositions containing same); U.S. Pat. No. 4,590,209 (Alkoxy-acyl carnitines and pharmaceutical compositions containing same); U.S. Pat. No. 4,567,200 (Esters of mercapto acyl-carnitines and pharmaceutical compositions containing same); U.S. Pat. No. 4,032,641 (Nicotinoyl carnitine derivatives); U.S. Pat. No. 4,551,477 (Esters of alkoxy-acylderivatives of carnitine and pharmaceutical compositions containing same); U.S. Pat. No. 4,401,827 (Novel acyl-derivatives of carnitine and process for their preparation); U.S. Pat. No. 5,260,464 (Carnitine derivatives, process for their preparation, and their use in human therapy); U.S. Pat. No. 4,859,698 (Novel class of acyl-derivatives of carnitine, process for preparing same and therapeutic use thereof); U.S. Pat. No. 4,692,543 (Optically-active di-[3-chloro-2-oxy-propyltrimethylammonium]-tartrate); U.S. Pat. No. 5,258,552 (N-alkylamides of d(+)-carnitine having antibacterial activity, process for their preparation and pharmaceutical and cosmetic compositions containing same); etc.

Similarly, a wide variety of mitochondrially active antioxidants (i.e. antioxidants which reduce the metabolic production of reactive oxygen species, as measured, for example by the oxidant production assay described below) and their methods of formulation, synthesis and production are known. Generally these include physiologically reactive thiols, preferably physiologically reactive sulfhydryl group containing compounds. Exemplary antioxidants include glutathione, NAC, lipoic acid, their derivatives, etc. For example, lipoic acid derivatives and their methods of production are well described, e.g. U.S. Pat. No. 5,621,117 (Method for the racemization of enantiomers of .alpha.-lipoic acid); U.S. Pat. No. 5,489,694 (Preparation of R/S-.gamma.-lipoic acid or R/S-.alpha.-lipoic acid); U.S. Pat. No. 5,463,093 (Palladium complexes and methods for using same in the treatment of tumors or Psoriasis); U.S. Pat. No. 5,334,612 (Pharmaceutical compositions containing as active substance sulphur-containing carboxylic acids and their use in combating retroviruses); U.S. Pat. No. 4,390,620 (Method and composition for the detection and study of cellular activity or the like and means for applying such method); U.S. Pat. No. 5,118,505 (Combination preparation for the treatment of nerve cell and nerve fibre diseases and injury); U.S. Pat. No. 4,767,704 (Protein-free culture medium), etc. In addition, we have found the R-enantiomeric form of lipoic especially suitable for preferential mitochondrial targeting.

Convenient assays for the requisite bioactivities are described above or in the references cited herein. For example, cardiolipin content is readily assayed as referenced in Guan, Z. Z., Soderberg, M., Sindelar, P., and Edlund, C. *Content and Fatty Acid Composition of Cardiolipin in the Brain of Patients with Alzheimer's Disease.* Neurochem. Int. 25: 295–300, 1994 and oxidant production (DCFH) may be assayed as described by LeBel, C. P., Ischiropoulos, H., and Bondy, S. C. *Evaluation of the Probe 2',7'-Dichlorofluorescin as an Indicator of Reactive Oxygen Species Formation and Oxidative Stress.* Chem. Res. Toxicol. 5: 227–231, 1992. Assays for parameters of aging such as host activity and behavior such as grooming, sexual activity, dominance, etc., coat condition, wound repair, including molecular lesions, muscle strength and tone, kidney appearance and function, etc. are similarly well known in the art.

The invention provides administratively convenient formulations of the compositions including dosage units incorporated into a variety of containers. Dosages of the carnitine and antioxidant are administered orally in the range of about 1 mg/kg to about 1 g/kg, preferably in the range of about 10 mg/kg to about 500 mg/kg more preferably in the range of about 20 mg/kg to about 200 mg/kg of body weight per day, although variations will necessarily occur depending on the formulation, host, etc. Convenient unit dosage containers and/or formulations include tablets, capsules, lozenges, troches, hard candies, powders, metered sprays, creams, suppositories, etc. The compositions may be combined with a pharmaceutically acceptable excipient such as gelatin, an oil, etc. and/or other pharmaceutically active agent(s). For example, the compositions may be advantageously combined and/or used in combination with other therapeutic or prophylactic agents, different from the subject compounds. In many instances, administration in conjunction with the subject compositions enhances the efficacy of such agents. For example, the compounds may be advantageously used in conjunction with other antioxidants, free radical scavengers; etc.; and mixtures thereof, see e.g. *Goodman & Gilman's The Pharmacological Basis of Therapeutics,* 9$^{th}$ Ed., 1996, McGraw-Hill. In another embodiment, the invention provides the subject compounds in the form of one or more pro-drugs, which can be metabolically converted to the subject compounds by the recipient host. A wide variety of pro-drug formulations are known in the art.

The following examples are offered by way of illustration and not by way of limitation.

EXAMPLES

Formulation 1. 250 mg pharmaceutical grade dry acetyl-L-carnitine and 250 mg pharmaceutical grade dry lipoic acid are administered orally 4× daily in 500 mg gelatin capsules.

Formulation 2. 500 mg pharmaceutical grade dry acetyl-L-carnitine and 300 mg pharmaceutical grade dry N-acetyl cysteine are administered orally 4× daily in 800 mg gelatin capsules.

Formulation 3. 1% w/v of each pharmaceutical grade acetyl-L-carnitine and pharmaceutical grade glutathione are administered orally in a 2% glucose solution to 0.2 and 0.1 g/kg/day total dosage.

Animal data reveal treated host cell mitochondria demonstrate enhanced levels of cardiolipin and membrane potential, reduced production of reactive oxygen species, and mitigation of indicia of aging, including activity, muscle tone, coat appearance and kidney morphology.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for increasing the metabolic rate of aged cells without a concomitant increase in metabolic production of reactive oxygen species, comprising orally administering to a mammalian host an effective dosage of at least about 10 mg/kg host/day of a carnitine and at least about 10 mg/kg host/day of a mitochondrially active antioxidant which physiologically comprises a metabolically reactive thiol group.

2. The method of claim 1 wherein the carnitine is acetyl-L-carnitine.

3. The method of claim 1 wherein the antioxidant comprises at least one of glutathione, N-acetyl cysteine and lipoic acid.

4. The method of claim 1 wherein the antioxidant is lipoic acid.

5. The method of claim 1 wherein the carnitine is acetyl-L-carnitine, the antioxidant is lipoic acid and the dosage is at least about 100 mg/kg host/day each.

6. An orally administratable dry unit dosage comprising at least about 250 mg of a carnitine and at least about 250 mg of a mitochondrially active antioxidant which physiologically comprises a metabolically reactive thiol group.

7. The dosage of claim 6 wherein the carnitine is acetyl-L-carnitine.

8. The dosage of claim 6 wherein the antioxidant comprises at least one of glutathione, N-acetyl cysteine and lipoic acid.

9. The dosage of claim 6 wherein the antioxidant is lipoic acid.

10. The dosage of claim 6 wherein the carnitine is acetyl-L-carnitine and the antioxidant is lipoic acid.

* * * * *

(12) EX PARTE REEXAMINATION CERTIFICATE (8907th)
United States Patent
Ames et al.

(10) Number: US 5,916,912 C1
(45) Certificate Issued: Mar. 20, 2012

(54) DIETARY COMPOSITION FOR ENHANCING METABOLISM AND ALLEVIATING OXIDATIVE STRESS

(75) Inventors: Bruce N. Ames, Berkeley, CA (US); Tory M. Hagen, Berkeley, CA (US)

(73) Assignees: The National Institutes of Health, Bethesda, MD (US); Regents of the University of California, Oakland, CA (US)

Reexamination Request:
No. 90/007,626, Jul. 13, 2005

Reexamination Certificate for:
Patent No.: 5,916,912
Issued: Jun. 29, 1999
Appl. No.: 08/874,467
Filed: Jun. 16, 1997

(51) Int. Cl.
*A61K 45/00* (2006.01)
*A61K 31/205* (2006.01)
*A61K 31/221* (2006.01)
*A61K 31/325* (2006.01)
*A61K 31/385* (2006.01)
*A61K 45/06* (2006.01)
*A61K 31/21* (2006.01)
*A61K 31/185* (2006.01)
*A61P 43/00* (2006.01)

(52) U.S. Cl. ..................... 514/440; 514/561
(58) Field of Classification Search .................. None
See application file for complete search history.

(56) References Cited

To view the complete listing of prior art documents cited during the proceeding for Reexamination Control Number 90/007,626, please refer to the USPTO's public Patent Application Information Retrieval (PAIR) system under the Display References tab.

*Primary Examiner* — Evelyn Huang

(57) ABSTRACT

The metabolic rate of aged cells of a mammalian host is enhanced without a concomitant increase in metabolic production of reactive oxygen species by orally administering to the host an effective dosage of a carnitine, such as acetyl-L-carnitine, and a mitochondrially active antioxidant, such as lipoic acid.

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 5 is confirmed.

Claims 1-4 and 6-10 are cancelled.

New claims 11-16 are added and determined to be patentable.

*11. The method of claim 1, wherein the antioxidant is N-acetylcysteine.*

*12. The method of claim 11, further comprising administering one other antioxidant.*

*13. The dry unit dosage according to claim 6, wherein the antioxidant is N-acetylcysteine.*

*14. The dry unit dosage of claim 13, further comprising one other antioxidant.*

*15. The dry unit dosage according to claim 13, wherein said unit dosage is in the form of tablets.*

*16. The dry unit dosage according to claim 13, wherein said unit dosage is in the form of capsules.*

* * * * *